(12) United States Patent
Doyle et al.

(10) Patent No.: US 7,824,662 B2
(45) Date of Patent: Nov. 2, 2010

(54) BODY WASH WITH SUNSCREEN

(75) Inventors: Michael Phillip Doyle, Carmel, CA (US); Royce Dale Lillard, Phoenix, AZ (US); Royce Dale Lillard, III, Phoenix, AZ (US); Richard J. Bertozzi, Marco Island, FL (US)

(73) Assignee: Arizona Sunwash LLC, Phoenix, AZ (US)

( * ) Notice: Subject to any disclaimer, the term of this patent is extended or adjusted under 35 U.S.C. 154(b) by 323 days.

(21) Appl. No.: 12/156,966

(22) Filed: Jun. 6, 2008

(65) Prior Publication Data

US 2008/0317688 A1 Dec. 25, 2008

Related U.S. Application Data

(60) Provisional application No. 60/933,539, filed on Jun. 6, 2007.

(51) Int. Cl.
*A61K 8/84* (2006.01)
*A61Q 19/10* (2006.01)
*A61Q 17/04* (2006.01)

(52) U.S. Cl. ............... 424/59; 424/64; 424/74; 424/70.31; 424/70.11; 510/159

(58) Field of Classification Search ............ None
See application file for complete search history.

(56) References Cited

U.S. PATENT DOCUMENTS

| | | | |
|---|---|---|---|
| 4,701,321 A | 10/1987 | Bernstein | |
| 4,933,174 A | 6/1990 | Bernstein | |
| 4,938,953 A | 7/1990 | Pena et al. | |
| 5,028,417 A | 7/1991 | Bhat et al. | |
| 5,186,928 A | 2/1993 | Birtwistle | |
| 5,215,749 A | 6/1993 | Nicoll et al. | |
| 5,372,804 A | 12/1994 | Khoshdel et al. | |
| 5,498,406 A | 3/1996 | Nearn et al. | |
| 5,585,104 A | 12/1996 | Ha et al. | |
| 5,770,183 A | 6/1998 | Linares | |
| 5,904,917 A | 5/1999 | Mattai et al. | |
| 5,912,002 A | 6/1999 | Grieveson et al. | |
| 5,961,961 A | 10/1999 | Dobkowski et al. | |
| 5,961,992 A | 10/1999 | Hardi et al. | |
| 5,989,529 A | 11/1999 | Kaplan | |
| 5,994,280 A | 11/1999 | Giret et al. | |
| 6,043,204 A | 3/2000 | Kaufman et al. | |
| 6,048,517 A | 4/2000 | Kaplan | |
| 6,197,281 B1 | 3/2001 | Stewart et al. | |
| 6,217,852 B1 | 4/2001 | Gildenberg et al. | |
| 6,224,852 B1 | 5/2001 | Morgan et al. | |
| 6,322,799 B1 | 11/2001 | Hardi et al. | |
| 6,362,146 B1 | 3/2002 | Macaulay | |
| 6,399,045 B1 | 6/2002 | Morgan et al. | |
| 6,517,816 B1 | 2/2003 | Gonzalez et al. | |
| 6,528,070 B1 | 3/2003 | Bratescu et al. | |
| 6,576,228 B1 | 6/2003 | Crookham et al. | |
| 6,645,511 B2 | 11/2003 | Aronson et al. | |
| 6,998,113 B1 | 2/2006 | Traynor et al. | |
| 7,001,592 B1 | 2/2006 | Traynor et al. | |
| 2001/0053348 A1 | 12/2001 | Stewart et al. | |
| 2001/0053753 A1 | 12/2001 | Engekhart | |
| 2002/0081274 A1 | 6/2002 | Fan et al. | |
| 2003/0133899 A1 | 7/2003 | Fan et al. | |
| 2003/0215479 A1 | 11/2003 | Sendelbach et al. | |
| 2004/0234467 A1 | 11/2004 | Ananthapadmanabhan et al. | |
| 2004/0234468 A1 | 11/2004 | Kerschner et al. | |
| 2005/0169855 A1 | 8/2005 | Hoop et al. | |
| 2005/0265936 A1 | 12/2005 | Knopf et al. | |
| 2006/0188457 A1 | 8/2006 | Traynor et al. | |
| 2006/0275233 A1* | 12/2006 | Fishman et al. | ............ 424/64 |

* cited by examiner

*Primary Examiner*—Johann R Richter
*Assistant Examiner*—Hong Yu

(57) ABSTRACT

There is provided a body wash composition that includes sun screen materials. The body wash composition is formulated so that it may be applied during normal hygiene activities, such as washing. However, the composition applies an effective of sun screen material to the body such that the sun screen continues to provide effective solar protection even after rinsing or washing of the human body. Further, the material is a non greasy, easy to apply material that may be used during showering activities in a manner similar to a bar soap or cleanser. The composition includes a variety of materials that assist in the processing and storage of the body wash. Effective amounts of solar protective material include octyl methoxycinamate, octyl salycilate, and titanium dioxide. Testing shows that the product provides a solar protective level of at least approximately 14 even after multiple rinsings.

9 Claims, No Drawings

BODY WASH WITH SUNSCREEN

CROSS REFERENCE TO RELATED APPLICATIONS

This application claims priority from the provisional patent application Ser. No. 60/933,539 filed Jun. 6, 2007 in the names of Michael Doyle, Dale Lillard, Trace Lillard and Richard Bertozzi, and entitled "Body Wash With Sunscreen," incorporated herein by reference.

FIELD OF THE INVENTION

The present invention relates to body wash compositions. More particularly the present invention relates to body wash compositions that include a sunscreen agent, and still more particularly the invention relates to sunscreen additives which will not easily wash off the host's body.

BACKGROUND OF THE INVENTION

Humans can suffer various deleterious effects from overexposure to sunlight, including sunburn, aging of skin, wrinkling, and an increased risk of skin cancer. To avoid these effects, individuals who will be exposed to long periods of sunlight can cover their skin with sunscreen materials.

Personal care products like body washes are becoming more popular in the United States and around the world. Desirable body wash compositions should meet a number of criteria. For example, to be acceptable to consumers, a body wash should have many or all of the following characteristics: attractive appearance, acceptable scent, good lather, ability to leave the skin feeling soft and smooth, i.e., provide a skin conditioning benefit, be gentle to the skin, be easy to use and rinse off easily. Finally, it is desirable that the product provide some protection against the harmful rays of the sun.

Many consumers are aware of the harmful effects of the ultraviolet rays of the sun. An increase in skin cancer and photo-aging of the skin from excessive exposure to the sun's rays is widely known. As a result, many forms of sunscreen products are sold to provide varying degrees of protection. However, despite these many product choices, often consumers fail to apply such products on a regular basis. They are viewed many times as being inconvenient. Most people bathe or shower frequently, especially in the United States. To have a product used routinely in the bath or shower that would provide some level of sunscreen protection, would be very convenient and highly desirable. Many products such as make-up, lip balm and even hair spray products now have SPF protection. Providing some level of protection from a body wash would be valuable.

Combining sunscreens and cleansers, both bars and liquids, has been attempted for quite some time. For example, Berstein (Jun. 12, 1990), in U.S. Pat. No. 4,933,174, describes a detergent (non-ionic and/or amphoteric) and sunscreen agents which claims to provide some amount of protection to the skin from ultraviolet light even after rinsing the product. However, it requires at least 12 applications to be effective.

Grieveson, et. al. (Aug. 26, 1997), in U.S. Pat. No. 5,661,189, describe a liquid cleansing and moisturizing composition that contains benefit agents among which are sunscreens.

Gildenberg, et. al. (Apr. 17, 2001), in U.S. Pat. No. 6,217,852, describe personal cleansing compositions having photoprotective agents that require at least one photo-protective agent to be encapsulated in a time-release capsule.

Kaufman and Dulak (Mar. 28, 2000), in U.S. Pat. No. 6,043,204, describe a body cleansing composition providing protection against sunburn after rinsing that requires at least one hydroxyethylated organic nitrogen compound fixative, a polymeric quaternary ammonium salt and at least one volatile organic liquid.

Morgan, et. al. (May 1, 2001 and Jun. 4, 2002), in U.S. Pat. Nos. 6,224,852 and 6,399,045, describe liquid sunscreen compositions which both deposit and lather well that require cationic polymer.

Crookham, et. al. (Jun. 10, 2003), in U.S. Pat. No. 6,576,228, describe personal wash sunscreen compositions which deposit and lather well that require water soluble sunscreens.

Traynor, et. al. (Feb. 14, 2006), in U.S. Pat. Nos. 6,998,113 and 7,001,592, describe body washes containing additives including sunscreens that are encapsulated in sol-gel microcapsules.

Nevertheless, in spite of all the above attempts, there remains an unmet need for an effective body wash and sunscreen combination. There exists a need for a product that would provide an effective level of sun block, particularly a level of sun block or sunscreen that is higher than existing formulations. Further, the body washes and sunscreen combination should remain effective even after rinsing. Moreover, the sun screening functionality should preferably remain effective even after multiple rinsings or washings. Additionally, it would be desired that a body wash and sunscreen product have a gentle or acceptable feel on the human skin. Still further, it would be desired that a combined body wash and sunscreen be packaged in a means that can be readily and easily delivered to a human consumer, in bar form preferably. Hence there has been identified a need to provide an improved product that combines body wash and sunscreen functionality. The present invention addresses one or more of these needs.

SUMMARY OF THE INVENTION

Attempts to make a body wash with sunscreen ingredients that would impart some level of ultraviolet radiation protection after normal use were numerous and unsuccessful. To determine if the concept was even possible, commercially purchased well known body wash and sunscreen products were combined with vigorous mixing to produce a viscous liquid. After use, it was determined that some level of SPF protection was possible. Thereafter, combinations of selected sunscreen ingredients and surfactant mixtures were made with emulsifiers and skin care ingredients. It was discovered that certain sunscreens, which are effective against both uv-a and uv-b rays, when combined with selected anionic, non-ionic and amphoteric surfactants and emulsifiers, produce a product which cleanses the body and provides SPF protection of 4 or greater after only 1-4 washes. Comments from several people who used the product indicated some protection after only a single use. Skin care ingredients were also added to leave the skin feeling soft and smooth. The product, despite containing up to 15% of primarily oil soluble sunscreens, lathered quite well and was stable. The product samples appear to be simple yet elegant. Achieving success in combining seemingly incompatible ingredients in a product that cleans yet deposits active materials was unexpected, especially after so many unsuccessful trials.

Unlike leave on products, measuring the benefit of sunscreen ingredients applied from a body wash depends heavily upon the method of application. Since a body wash is generally used in the shower, the proper method of applying the product should be in the same manner as one would apply and use a bar of soap or liquid cleanser. Determining SPF of products prior to this invention used in-vitro methods (U.S.

Pat. No. 6,576,228) or modified procedures from those outlined in the Federal Register volume 43 (1978) pages 38264-267 for measurement of SPF (FDA monograph C.F.R. 21). For example, in U.S. Pat. Nos. 6,224,852 and 6,399,045, a 50 square cm area of the back was used to apply and rinse the product and test for SPF. Likewise, in U.S. Pat. Nos. 6,998,113 and 7,001,592 a 50 square cm area of the test site was used for applying the product, rinsing it and exposing it to radiation per the FDA monograph. It should be noted that when the product of this invention was tested using this method on a small 5 person panel, the average SPF value obtained was 3 times higher than when the product was used normally.

There is now provided a body wash composition that includes sun screen materials. The body wash composition is formulated so that it may be applied during normal hygiene activities, such as washing. However, the composition applies an effective of sun screen material to the body such that the sun screen continues to provide effective solar protection even after rinsing or washing of the human body. Further, the material is a non greasy, easy to apply material that may be used during showering activities in a manner similar to a bar soap or cleanser. The composition includes a variety of materials that assist in the processing and storage of the body wash. Effective amounts of solar protective material include octyl methoxycinnamate, octyl salycilate, and titanium dioxide. Testing shows that the product provides a solar protective level of at least approximately 14 even after multiple rinsings.

Other independent features and advantages of the body wash with sunscreen will become apparent from the following detailed description, taken in conjunction with the accompanying drawings which illustrate, by way of example, the principles of the invention.

DETAILED DESCRIPTION OF A PREFERRED EMBODIMENT

The following detailed description of the invention is merely exemplary in nature and is not intended to limit the invention or the application and uses of the invention. Furthermore, there is no intention to be bound by any theory presented in the preceding background of the invention or the following detailed description of the invention. Reference will now be made in detail to exemplary embodiments of the invention.

The following are examples of a composition with a body wash also containing sunscreen ingredients. A variety of surfactants may be used for the cleansing component and would be known to those skilled in the art. Likewise, other emulsifiers, carefully selected, could be used to create a stable product. A wide variety of skin care ingredients could also be used and would be known to those skilled in the art. Finally, sunscreen agents should preferably be organic compounds of limited water solubility and include both uv-a and uv-b protection materials.

Phase I

Heat water to 160 F., the add components 2, 3 and 4. Mix for 2 minutes. Add component 5 and homogenize until there are no lumps. This will take about 20 minutes. Then add component 6 and mix for 10 minutes. The ending temperature should be about 135 F. Set aside.

| Order | Component | Chemical Name | % BY Wt. |
|---|---|---|---|
| 1 | De-ionized water | De-ionized water | 43.30 |
| 2 | Versene 220 | Tetrasodium ethylenediaminetertraacetate tetrahydrate | 0.20 |
| 3 | Gemaben II | Propylene Glycol (and) Diazolidlnyl Urea (and) Methylparaben | 1.00 |
| 4 | PEG 400 | PEG 400 | 2.00 |
| 5 | Carbopol 940 | Carbomer | 0.40 |
| 6 | Sulfochem B-DEV | Sodium Laureth Sulfate (and) Cocamide DEA (and) Cocamidopropyl Betaine | 30.00 |

Phase II

Combine components 7, 8, 9, 10, 11 and 12 while heating to about 130 F. to homogenize. Then add component 13, mix for 5 minutes. Then add component 14, mix for 5 minutes. Set aside.

| Order | Component | Chemical Name | % BY Wt. |
|---|---|---|---|
| 7 | Lauric acid | Dodecanoic Acid | 1.50 |
| 8 | Soy Oil | Soy Oil | 1.50 |
| 9 | Homosalate | 3,3,5-Trimethylcyclohexyl 2-hydroxybenzoate | 4.00 |
| 10 | Octyl methoxycinnamate | Octyl methoxycinnamate | 3.75 |
| 11 | Oxybenzone | Benzophenone-3 | 3.00 |
| 12 | Octyl salycilate | Octyl salycilate | 2.50 |
| 13 | Ariacel P-135 | PEG-30 Dipolyhydroxystearate | 0.10 |
| 14 | Titanium dioxide | Titanium dioxide | 0.10 |

At this point the oil phase material is combined with the water phase material. Make an emulsion. Phase 1 should be about 135 F. Phase 2 should be about 130 F. Mill for approximately 10-15 min.

Phase III

Heat water, component 15, to 185 F. Add component 16 and mix till dissolved. Add to the emulsion above and mix till dissolved. Mix till temp drops to 110 F. and add component 17. Mix till temp is 105 F.

| Order | Component | Chemical Name | % BY Wt. |
|---|---|---|---|
| 15 | De-ionized water | De-ionized water | 6.00 |
| 16 | RitaPro 165 | Glyceryl stearate (and) PEG 100 Stearate | 0.30 |
| 17 | Fragrance - Herbal | Fragrance | 0.35 |

The completed product should be off white and smooth.

Range of material. The following chart lists the materials from the above composition and also provides a range by weight percentage for the materials.

| Order | Component | Chemical Name | Wt % Range |
|---|---|---|---|
| 1 | De-ionized water | De-ionized water | |
| 2 | Versene 220 | Tetrasodium ethylenediaminetertraacetate tetrahydrate | 0.15-0.45 |

-continued

| Order | Component | Chemical Name | Wt % Range |
|---|---|---|---|
| 3 | Gemaben II | Propylene Glycol (and) Diazolidlnyl Urea (and) Methylparaben | 0.75-1.50 |
| 4 | PEG 400 | PEG 400 | 1.00-2.50 |
| 5 | Carbopol 940 | Carbomer | 0.20-1.00 |
| 6 | Sulfochem B-DEV | Sodium Laureth Sulfate (and) Cocamide DEA (and) Cocamidopropyl Betaine | 10.00-60.00 |
| 7 | Lauric acid | Dodecanoic Acid | 0.50-3.00 |
| 8 | Soy Oil | Soy Oil | 0.50-3.00 |
| 9 | Homosalate | 3,3,5-Trimethylcyclohexyl 2-hydroxybenzoate | 2.00-6.00 |
| 10 | Octyl methoxycinnamate | Octyl methoxycinnamate | 2.00-6.00 |
| 11 | Oxybenzone | Benzophenone-3 | 2.00-6.00 |
| 12 | Octyl salycilate | Octyl salycilate | 2.00-6.00 |
| 13 | Arlacel P-135 | PEG-30 Dipolyhydroxystearate | 0.10-1.00 |
| 14 | Titanium dioxide | Titanium dioxide | 0.11-1.00 |
| 15 | De-ionized water | De-ionized water | |
| 16 | RitaPro 165 | Glyceryl stearate (and) PEG 100 Stearate | 0.10-1.50 |
| 17 | Fragrance - Herbal | Fragrance | 1.10-1.50 |

The Arlacel in the above formulations can be substituted or eliminated. In a first optional formulation, the amount of Arlacel is substituted with a blend of 60 wt % sorbitan monosterate and 40 wt % sorbitan monopalmitate. The monosterate is available under the trade name Span 60 from Uniqema Americas, and the monopalmitate is sold under the trade name Span 40 also from Uniqema Americas.

In a second optional formulation, the Arlacel is substituted by a blend of 55 wt % sorbitan monolaurate and 45 wt % sorbitan trioleate. These materials are sold under the trade names span 20 and Span 85 respectively, again offered by Uniqema Americas.

A second preferred embodiment is prepared in the following steps and formulation.

Phase I

Heat water to 160 F., the add components 2, 3 and 4. Mix for 2 minutes. Add component 5 and homogenize until there are no lumps. This will take about 20 minutes. Then add component 6 and mix for 10 minutes. The ending temperature should be about 135 F. Set aside.

| Order | Component | Chemical Name | % BY Wt. |
|---|---|---|---|
| 1 | De-ionized water | De-ionized water | 41.10 |
| 2 | Versene 220 | Tetrasodium ethylenediaminetertraacetate tetrahydrate | 0.20 |
| 3 | Gemaben II | Propylene Glycol (and) Diazolidlnyl Urea (and) Methylparaben | 1.00 |
| 4 | PEG 400 | PEG 400 | 2.00 |
| 5 | Carbopol 940 | Carbomer | 0.40 |
| 6 | Sulfochem B-DEV | Sodium Laureth Sulfate (and) Cocamide DEA (and) Cocamidopropyl Betaine | 31.00 |

Phase II

Combine components 7, 8, 9, 10, 11 and 12 while heating to about 130 F. to homogenize. Then add component 13, mix for 5 minutes. Then add component 14, mix for 5 minutes. Set aside.

| Order | Component | Chemical Name | % BY Wt. |
|---|---|---|---|
| 7 | Lauric acid | Dodecanoic Acid | 1.50 |
| 8 | Soy Oil | Soy Oil | 1.00 |
| 9 | Homosalate | 3,3,5-Trimethylcyclohexyl 2-hydroxybenzoate | 4.00 |
| 10 | Octyl methoxycinnamate | Octyl methoxycinnamate | 3.75 |
| 11 | Oxybenzone | Benzophenone-3 | 3.00 |
| 12 | Octyl salycilate | Octyl salycilate | 2.50 |
| 13 | Span 20 | Sorbitan Monolaurate | 0.055 |
| 14 | Span 85 | Sorbitan Trioleate | 0.045 |
| 15 | Titanium dioxide | Titanium dioxide | 2.00 |

At this point the oil phase material is combined with the water phase material. Make an emulsion. Phase 1 should be about 135 F. Phase 2 should be about 130 F. Mill for approximately 10-15 min.

Phase III

Heat water, component 16, to 165 F. Add component 17 and mix till dissolved. Add to the emulsion above and mix till dissolved. Mix till temp drops to 110 F. and add component 18. Mix till temp is 105 F. The completed product should be off white in color and should be smooth in texture.

| Order | Component | Chemical Name | % BY Wt. |
|---|---|---|---|
| 16 | De-ionized water | De-ionized water | 6.00 |
| 17 | RitaPro 165 | Glyceryl stearate (and) PEG 100 Stearate | 0.30 |
| 18 | Fragrance - Herbal | Fragrance | 0.34 |

Range of material. The following chart lists the materials from the above composition and also provides a range by weight percentage for the materials.

| Order | Component | Chemical Name | Wt % Range |
|---|---|---|---|
| 1 | De-ionized water | De-ionized water | |
| 2 | Versene 220 | Tetrasodium ethylenediaminetertraacetate tetrahydrate | 0.15-0.45 |
| 3 | Gemaben II | Propylene Glycol (and) Diazolidlnyl Urea (and) Methylparaben | 0.75-1.50 |
| 4 | PEG 400 | PEG 400 | 1.00-2.50 |
| 5 | Carbopol 940 | Carbomer | 0.20-1.00 |
| 6 | Sulfochem B-DEV | Sodium Laureth Sulfate (and) Cocamide DEA (and) Cocamidopropyl Betaine | 10.00-60.00 |
| 7 | Lauric acid | Dodecanoic Acid | 0.50-3.00 |
| 8 | Soy Oil | Soy Oil | 0.50-3.00 |
| 9 | Homosalate | 3,3,5-Trimethylcyclohexyl 2-hydroxybenzoate | 2.00-6.00 |
| 10 | Octyl methoxycinnamate | Octyl methoxycinnamate | 2.00-6.00 |
| 11 | Oxybenzone | Benzophenone-3 | 2.00-6.00 |
| 12 | Octyl salycilate | Octyl salycilate | 2.00-6.00 |
| 13 | Span 20 | Sorbitan Monolaurate | 0.10-1.00 |
| 14 | Span 85 | Sorbitan Trioleate | 0.10-1.01 |
| 15 | Titanium dioxide | Titanium dioxide | 0.0-4.00 |
| 16 | De-ionized water | De-ionized water | |
| 17 | RitaPro 165 | Glyceryl stearate (and) PEG 100 Stearate | 0.10-1.50 |
| 18 | Fragrance - Herbal | Fragrance | 1.10-1.50 |

Testing Method of Present Invention

The product of this invention was tested by an independent testing laboratory following Good Laboratory Practices and was based on the method outlined in the Food and Drug Administration (FDA) Final Monograph for sunscreen testing published in the Federal Register, Vol. 64, No. 98, May 21, 1999. Concurrently with the test material, a standard sunscreen preparation of 8% Homosalate with a mean SPF value of 4.47+/−1.28 was tested.

Test subjects (20) were assigned either the test product or an unidentified well known commercially available body wash according to a generated randomization schedule. They were instructed to discontinue the use of their regular cleansing and/or body wash products. All subjects were advised not to introduce any new personal care products, moisturizers or cosmetics during the study interval. They used the products during morning showering for three mornings in succession, washing and rinsing as with any liquid body wash. This was accomplished by working the product into a lather applying by hand, sponge or wash cloth. After showering again with the product on the fourth morning, they were tested after 1 hour. Prior to receiving the alternate test product, all subjects used their regular cleansing products for 5 consecutive days as a rest interval. Results indicated an average SPF value for the test product of 4.74+/−0.54.

The sunscreen/body wash was tested for SPF capability as follows: 50 cm$^2$ of testing site was wetted with 10 ml of water delivered with a syringe. The test sample was applied as per FDA monograph C.F.R. 21 to the area. Lather was worked into the subject for 3 minutes to allow the product to absorb into the skin. The area was rinsed after 2 additional minutes with 20 ml of water, then the area was patted dry and allowed 15 minutes before exposure to radiation as per FDA monograph. The skin was exposed to UV radiation and the MED was noted and compared to the MED for skin without treatment. Results are shown in the following tables.

TABLE 1

Individual SPF Values

| Subject Number | Subject Initials | Subject ID # | Skin Type | Age | Sex | 8% HMS Standard | Sample #6234 Body Wash |
|---|---|---|---|---|---|---|---|
| 1 | * | * | * | * | * | * | * |
| 2 | EA | 8026 | III | 56 | F | 4.4 | 5.0 |
| 3 | JS | 15288 | III | 26 | F | 4.4 | 4.5 |
| 4 | DD | 15575 | II | 51 | M | 4.4 | 5.0 |
| 5 | JM | 52377 | II | 39 | M | 5.0 | 4.0 |
| 6 | LS | 6974 | III | 59 | F | 4.4 | 5.0 |
| 7 | TL | 23195 | III | 39 | M | 5.0 | 5.0 |
| 8 | MM | 33356 | II | 41 | F | 4.0 | 4.0 |
| 9 | BR | 13187 | II | 54 | F | 5.0 | 4.5 |
| 10 | VT | 16578 | III | 40 | F | 5.0 | 4.5 |
| 11 | DT | 11721 | II | 46 | F | 5.0 | 6.3 |
| 12 | KT | 207 | II | 34 | F | 4.4 | 5.0 |
| 13 | DM | 53579 | II | 50 | F | 5.0 | 4.5 |
| 14 | GM | 31667 | II | 39 | F | 5.0 | 4.5 |
| 15 | CS | 27351 | II | 57 | F | 4.4 | 4.5 |
| 16 | KP | 50612 | III | 45 | F | 5.0 | 4.5 |
| 17 | AH | 39455 | III | 39 | F | 4.4 | 4.5 |
| 18 | RL | 53968 | III | 52 | M | 5.0 | 5.0 |
| 19 | MR | 494 | II | 51 | F | 5.0 | 4.0 |
| 20 | TP | 12791 | II | 52 | M | 5.0 | 5.0 |
| 21 | CM | 42362 | II | 48 | F | 5.0 | 5.5 |
| Average SPF (n = 20) | | | | | | 4.74 | 4.74 |
| Standard Deviation | | | | | | 0.34 | 0.54 |
| Standard Error | | | | | | 0.08 | 0.12 |
| t (one-tail) | | | | | | 1.729 | 1.729 |
| A | | | | | | 0.13 | 0.21 |
| SPF Label | | | | | | 4.61 | 4.53 |

TABLE 2

Individual SPF Values

| Subject Number | Subject Initials | Subject ID # | Skin Type | Age | Sex | 8% HMS Standard | Sample #6234 Body Wash |
|---|---|---|---|---|---|---|---|
| 1 | SA | 9644 | II | 43 | F | 4.4 | 18.0 |
| 2 | CM | 18105 | II | 51 | F | 4.0 | 13.7 |
| 3 | VS | 8800 | III | 55 | F | 4.4 | 15.0 |
| 4 | ML | 7123 | II | 44 | F | 4.0 | 13.7 |
| 5 | PN | 52982 | II | 51 | F | 4.4 | 15.0 |
| Average SPF (n = 5) | | | | | | 4.24 | 15.08 |
| Standard Deviation | | | | | | 0.22 | 1.76 |
| Standard Error | | | | | | 0.10 | 0.79 |
| t (one-tail) | | | | | | 2.132 | 2.132 |
| A | | | | | | 0.21 | 1.68 |
| SPF Value | | | | | | 4 | 13 |

This Example demonstrates that the sunscreen/body wash enhanced the sun protection as measured by this protocol, as compared to untreated skin, by an average SPF of over 18.

Testing was also performed on the second preferred formulation. The second formulation achieved an SPF score of between approximately 12 and 16. It is further to be appreciated that the second formulation was tested under procedures wherein the body wash composition was applied during a cleansing procedure such as showering, and the applied material was also subjected to multiple rinsings. However, the measured SPF score was still recorded at between 12 and 16 even after such washings and rinsings. It is not believed that other products now commercially available are measured in this manner. Thus, the preferred formulation achieves an effective level of measured sun blockage even after rinsings.

Equipment to prepare the formulations noted herein may be taken from commonly available laboratory and commercial suppliers. Commonly used equipment includes blenders, mixers, grinders, and heaters along with variously sized storage and mixing containers. Other processing equipment for loading the finished product into desired retail containers may also be used.

The materials to manufacture the formulations noted herein are also taken from publicly available commercial suppliers. In certain instances materials are commonly referred to by various trade names, and this has been noted, e.g., "Versene", "GermabenII", "Carbopol", "Sulfochem B-DEV", and "Span" products. These materials may be acquired from various suppliers known to people skilled in the art. Other materials are commonly referred to by their chemical names, e.g., soy, titanium dioxide, and water, and are so noted.

A key advantage of the body wash with sunscreen described herein relates to the manner of usage that the composition allows. The body wash composition may be applied by the human user during normal hygiene activities such as washing and/or showering. An effective amount of solar protective material remains on the user's skin even after the rinsing and washing has been completed. Thus, the user has applied to himself or herself an amount of solar protective material during normal washing activities such as the morning shower. An additional or separate step of applying a greasy, sunblocking material is not required. The user can thus proceed through his daily activities such as recreation with the sunscreen material now applied to the body. Furthermore, and importantly, the testing described above indicates that an effective level of sunblocking material remains on the user's skin even after multiple rinsings. Thus, the user can confidently pursue activities such as water sports or exercises or any activity which might cause the user to perspire, and an effective level of sunscreen material will remain. Thus, it is believed that the compositions and formulations described herein provide an improved and convenient method for an active person to apply sunscreen material.

While the invention has been described with reference to a preferred embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to a particular embodiment disclosed as the best mode contemplated for carrying out this invention, but that the invention will include all embodiments falling within the scope of the appended claims.

What is claimed is:

1. A combined body wash and sunscreen formulation comprising the combination of the following materials in the approximate weight percentages at both the lower and upper range:

| Chemical Name | Wt % Range |
| --- | --- |
| De-ionized water | balance |
| Tetrasodium ethylenediaminetertraacetate tetrahydrate | 0.15-0.45 |
| Propylene Glycol (and) Diazolidlnyl Urea (and) Methylparaben | 0.75-1.50 |
| PEG 400 | 1.00-2.50 |
| Carbomer | 0.20-1.00 |
| Sodium Laureth Sulfate (and) Cocamide DEA (and) Cocamidopropyl Betaine | 10.00-60.00 |
| Dodecanoic Acid | 0.50-3.00 |
| Soy Oil | 0.50-3.00 |
| 3,3,5-Trimethylcyclohexyl 2-hydroxybenzoate | 2.00-6.00 |
| Octyl methoxycinnamate | 2.00-6.00 |
| Benzophenone-3 | 2.00-6.00 |
| Octyl salycilate | 2.00-6.00 |
| Sorbitan monolaurate | 0.10-1.00 |
| Sorbitan trioleate | 0.10-1.01 |
| Titanium dioxide | 0.11-1.00 |
| Glyceryl stearate (and) PEG 100 Stearate | 0.10-1.50. |

2. The combined body wash and sunscreen formulation according to claim 1 further comprising fragrance in the amount of approximately 1.10 to approximately 1.50 wt %.

3. The combined body wash and sunscreen formulation according to claim 2 wherein the materials are present in substantially the amounts indicated:

| Chemical Name | Wt % Range |
| --- | --- |
| De-ionized water | balance |
| Tetrasodium ethylenediaminetertraacetate tetrahydrate | 0.20 |
| Propylene Glycol (and) Diazolidlnyl Urea (and) Methylparaben | 1.0 |
| PEG 400 | 2.00 |
| Carbomer | 0.40 |
| Sodium Laureth Sulfate (and) Cocamide DEA (and) Cocamidopropyl Betaine | 30.00 |
| Dodecanoic Acid | 1.50 |
| Soy Oil | 1.50 |
| 3,3,5-Trimethylcyclohexyl 2-hydroxybenzoate | 4.00 |
| Octyl methoxycinnamate | 3.75 |
| Benzophenone-3 | 3.00 |
| Octyl salycilate | 2.50 |
| Sorbitan monolaurate | 0.055 |
| Sorbitan trioleate | 0.045 |
| Titanium dioxide | 0.10 |
| Glyceryl stearate (and) PEG 100 Stearate | 0.30 |
| Fragrance | 0.35. |

4. A combined body wash and sunscreen formulation comprising:

| Chemical Name | Wt % Range |
| --- | --- |
| De-ionized water | balance |
| Tetrasodium ethylenediaminetertraacetate tetrahydrate | 0.15-0.45 |
| Propylene Glycol (and) Diazolidlnyl Urea (and) Methylparaben | 0.75-1.50 |
| PEG 400 | 1.00-2.50 |
| Carbomer | 0.20-1.00 |
| Sodium Laureth Sulfate (and) Cocamide DEA (and) Cocamidopropyl Betaine | 10.00-60.00 |
| Dodecanoic Acid | 0.50-3.00 |
| Soy Oil | 0.50-3.00 |
| 3,3,5-Trimethylcyclohexyl 2-hydroxybenzoate | 2.00-6.00 |
| Octyl methoxycinnamate | 2.00-6.00 |
| Benzophenone-3 | 2.00-6.00 |
| Octyl salycilate | 2.00-6.00 |
| Sorbitan monolaurate and sorbitan trioleate | 0.10-1.00 |
| Titanium dioxide | 0.11-1.01 |
| Glyceryl stearate (and) PEG 100 Stearate | 0.10-1.50. |

5. The combined body wash and sunscreen formulation according to claim 4 wherein the sorbitan monolaurate and sorbitan trioleate are present in weight ratios of approximately 55:54.

6. The combined body wash and sunscreen formulation according to claim 5 further comprising fragrance in a weight percentage of between approximately 1.10 and 1.50.

7. A combined body wash and sunscreen formulation comprising by weight percent:

| Chemical Name | Wt % Range |
| --- | --- |
| De-ionized water | balance |
| Tetrasodium ethylenediaminetertraacetate tetrahydrate | 0.15-0.45 |
| Propylene Glycol (and) Diazolidlnyl Urea (and) Methylparaben | 0.75-1.50 |
| PEG 400 | 1.00-2.50 |
| Carbomer | 0.20-1.00 |

-continued

| Chemical Name | Wt % Range |
|---|---|
| Sodium Laureth Sulfate (and) Cocamide DEA (and) Cocamidopropyl Betaine | 10.00-60.00 |
| Dodecanoic Acid | 0.50-3.00 |
| Soy Oil | 0.50-3.00 |
| 3,3,5-Trimethylcyclohexyl 2-hydroxybenzoate | 2.00-6.00 |
| Octyl methoxycinnamate | 2.00-6.00 |
| Benzophenone-3 | 2.00-6.00 |
| Octyl salycilate | 2.00-6.00 |
| Sorbitan monolaurate and sorbitan trioleate | 0.10-1.00 |

-continued

| Chemical Name | Wt % Range |
|---|---|
| Titanium dioxide | 0.11-1.00 |
| Glyceryl stearate (and) PEG 100 Stearate | 0.10-1.50. |

8. The combined body wash and sunscreen formulation according to claim 7 wherein the sorbitan monolaurate and sorbitan trioleate are present in weight ratios of approximately 55:54.

9. The combined body wash and sunscreen formulation according to claim 8 further comprising fragrance in a weight percentage of between approximately 1.10 and 1.50.

* * * * *